(12) United States Patent
Wimmer et al.

(10) Patent No.: US 6,689,559 B2
(45) Date of Patent: Feb. 10, 2004

(54) EFFICIENT HEPATITIS C VIRUS REPLICON AND ITS USE IN IDENTIFYING ANTIVIRAL COMPOUNDS

(75) Inventors: Eckard Wimmer, East Setauket, NY (US); Chengyu Liang, Stony Brook, NY (US); Sung Key Jang, Kyungbuk (KR); Bumsuk Hahm, San Diego, CA (US)

(73) Assignee: The Research Foundation of the State University of New York, Albany, NY (US)

( * ) Notice: Subject to any disclaimer, the term of this patent is extended or adjusted under 35 U.S.C. 154(b) by 0 days.

(21) Appl. No.: 09/998,900

(22) Filed: Nov. 29, 2001

(65) Prior Publication Data

US 2002/0098202 A1 Jul. 25, 2002

(51) Int. Cl.⁷ .............................. C12Q 1/70; C12N 5/10
(52) U.S. Cl. .................. 435/5; 435/91.1; 435/69.3; 435/455; 435/475; 435/370; 536/23.72
(58) Field of Search .................. 435/5, 69.1, 69.3, 435/455, 475, 370; 536/23.72

(56) References Cited

U.S. PATENT DOCUMENTS

| | | | |
|---|---|---|---|
| 5,401,629 A | 3/1995 | Harpold et al. | |
| 6,130,036 A | 10/2000 | Loeb et al. | |
| 6,153,421 A | 11/2000 | Yanagi et al. | |
| 6,225,045 B1 | 5/2001 | Karn et al. | |
| 6,392,028 B1 * | 5/2002 | Rice, III et al. | 536/23.72 |

FOREIGN PATENT DOCUMENTS

EP 1043399 A2 11/2000

OTHER PUBLICATIONS

V. Lohmann, F. Körner, J.–O. Koch, U. Herian, L. Theilmann, R. Bartenschlager, "Replication of Subgenomic Hepatitis C Virus RNAs in a Hepatoma Cell Line" *Science* 285:110–113 (1999).

Masayuki Yanagi, Robert H. Purcell, Suzanne U. Emerson, and Jens Bukh, "Transcripts from a single full–length cDNA clone of hepatitis C virus are infectious when directly transfected into the liver of a chimpanzee," *Proc. Natl. Acad. Sci. USA* 94:8738–8743 (1997).

Ilya Frolov, Eugene Agapov, Thomas A. Hoffman, Jr., Béla M. Prágai, Mara Lippa, Sondra Schlesinger, and Charles M. Rice, "Selection of RNA Replicons Capable of Persistent Noncytopathic Replication in Mammalian Cells," *Journal of Virology* 73: 3854 3865 (1999).

Ralf Bartenschlager and Volker Lohmann, "Replication of hepatitis C virus," *Journal of General Virology* 81: 1631–1648 (2000).

Ralf Bartenschlager and Volker Lohmann, "Novel cell culture systems for the hepatitis C virus," *Antiviral Research* 52: 1–17 (2001).

Robert E. Lanford, Helen Lee, Deborah Chavez, Bernadette Guerra and Kathleen M. Brasky, "Infectious cDNA clone of the hepatitis C virus genotype 1 prototype sequence," *Journal of General Virology* 82: 1291–1297 (2001).

* cited by examiner

Primary Examiner—Donna C. Wortman
(74) Attorney, Agent, or Firm—Hoffman & Baron, LLP (57) ABSTRACT

The present invention provides a Hepatitis C Virus (HCV) replicon that efficiently replicates in an eukaryotic cell. The HCV replicon includes a nucleic acid sequence encoding a subgenomic fragments of HCV of any genotype that confer on the RNA the ability to replicate, and a nucleic acid sequence encoding an acetyl transferase selectable marker, such as puromycin. Also provided is an HCV type 1a replicon that efficiently replicates in an eukaryotic cell and includes a nucleic acid sequence encoding subgenomic fragments of type 1a HCV that confer on the RNA the ability to replicate, and a nucleic acid sequence encoding a acetyl transferase selectable marker. Further provided are eukaryotic cell lines that include an HCV replicon or an HCV type 1a replicon which efficiently replicate in the eukaryotic cell. The present invention also provides screening methods for identifying candidate compounds that inhibit the propagation of HCV.

12 Claims, 7 Drawing Sheets

EFFICIENT HEPATITIS C VIRUS REPLICON AND ITS USE IN IDENTIFYING ANTIVIRAL COMPOUNDS

This work was supported in part by grant awards R37 AI15122 and R01 AI32100 from the National Institutes of Health. The government may have certain rights in this invention.

BACKGROUND

The hepatitis C virus (HCV) is the sole member of the genus Hepacivirus of the family Flaviviridae, which also includes the Flavivirus, yellow fever virus and the Pestivirus, bovine viral diarrhea virus. Since the discovery of HCV in 1989, the viral genome has been well characterized. The genome is a positive-sense single-stranded RNA of about 9.3 kb, that consists of a single open reading frame (ORF) and nontranslated regions (NTRs) at the 5' and 3' ends (Bartenschlager and Lohmann, 2000).

The 5'NTR is highly structured and contains an internal ribosomal entry site (IRES) that mediates cap-independent translation of the viral polyprotein. The 3'NTR is tripartite and is composed of a short variable region (~21–39 nucleotides), a poly (U) tract of variable length, and a highly conserved terminal sequence of 98 nucleotides.

The ORF of HCV is translated into a polyprotein (i.e., $NH_2$-core-E1-E2-p7-NS2-NS3-NS4A-NS4B-NS5A-NS5B-COOH) that is co-translationally and posttranslationally processed by host cell and viral proteases into at least 10 distinct products. The core and envelope (E1 and E2) proteins are the major viral constituents of the virus particle while the remainder, the non-structural (NS) proteins, are required for virus replication.

NS2 forms an autoprotease with the amino terminus of NS3. NS3 is a bifunctional molecule with serine proteinase and NTPase/helicase activities. NS4A is a cofactor of the NS3 proteinase. The functions of NS4B and p7 proteins are so far unknown. NS5B is identified as the RNA-dependent RNA polymerase (RdRp). NS5A is highly phosphorylated and contains the interferon sensitivity-determining region (ISDR), which appears to be involved in resistance of the virus to interferon treatment.

HCV replication involves the generation of antisense strand RNA intermediates, which serve as the template for synthesis of the genomic RNA. Replication is catalyzed by the cytoplasmic membrane-associated replicase complex, which is thought to contain NS5B and other NS proteins (Bartenschlager and Lohmann, 2000). However, despite the well-characterized viral genome of HCV, the individual steps underlying RNA replication are largely unknown.

RNA viruses, such as HCV, are quasispecies due to the error rate of RNA synthesis and absence of proof reading and editing functions. RNA viruses are genetic mixtures of which the "wild type" is the genotype replicating best under a fixed set of conditions. With most RNA viruses, the "wild type" efficiently outcompetes other genotypes (giving the impression of genetic purity). However, many genotypes can coexist in a host organism, giving rise to great genetic diversity. Different sets of genotypes occur in different geographical regions. Thus, a remarkable characteristic of HCV is its genetic heterogeneity.

Currently, at least six major genotypes (genotypes 1–6) each containing a number of subtypes (1a, 1b, 1c, 2a, 2b, 2c etc.) have been described (Zein and Persing et al., 1996). Subtypes 1a and 1b account for the majority of HCV infections in the United States, Europe, and Japan (Zein and Rakela et al., 1996). For example, HCV1a accounts for over 50% of HCV infections in the United States and approximately 30% of HCV infections in Europe and also in South America. In contrast, a low prevalence of infection with HCV1a occurs in Asia and Japan.

HCV subtype 1b accounts for about 70% of HCV infections in Asia and in Japan. Interestingly, HCV subtypes 1a and 1b do not appear to exist in HCV infections in the North African sub-continent.

The sequence similarity between 1a and 1b is approximately 81% based on the genomic variability in a 222-nucleotide segment of NS5 region. A number of studies have suggested that HCV genotype status may associate with the progression of liver disease, the outcome of HCV infection, and the response to interferon therapy (Bukh and Miller, 1995; Farci et al., 1997). Therefore, basic molecular studies would be valuable to define unique virological features for each of the HCV genotypes.

The recent availability of various infectious HCV cDNA clones provides a starting base for performing reverse genetics. However, due to a lack of an effective tissue culture system, the testing of mutant HCV clones has been restricted to the inoculation of chimpanzees. Numerous attempts have been undertaken to propagate HCV in cell culture systems including: (i) cultivation of hepatocytes from experimentally infected chimpanzees or from chronically infected patients; (ii) infection of primary cell lines with high-titer HCV-containing sera; (iii) transfection of human hepatocyte or non-hepatocyte cell lines with synthetic HCV RNA, etc. For a review of many of these attempts, see Bartenschlager and Lohmann, 2000.

The majority of these attempts have been unsuccessful. Further, even the few reports claiming sustained viral replication in cell culture systems showed poor reproducibility and a low level of replication (Dash et al., 1997). Detection of HCV RNA mostly depends on highly sensitive reverse-transcription RT-PCR assays, which is also error-prone due to carryover and sample-to-sample contamination.

Another approach was the establishment of a selectable HCV replicon derived from the HCV consensus genome of subtype 1b (Lohmann et al., 1999). This selectable HCV1b replicon is capable of autonomous replication in human hepatoma cell line Huh-7. This subgenomic HCV1b replicon lacks the structural regions and expresses the selectable marker neo, which confers resistance to neomycin sulfate (G418), which is toxic to normal cells (Southern, 1982). Resistance to neomycin sulfate is conferred by a phosphotransferase (neomycin phosphotransferase).

Upon transfection of the Huh-7 cells with the HCV1b replicon containing the neo selectable marker, a low number of colonies was obtained after selection with neomycin sulfate. Cell lines derived from these colonies contained actively replicating viral RNAs with 1000–5000 RNA molecules per cell. However, long-term follow-up studies showed that viral RNA replication relies on continuous selection and was strongly influenced by cell density and cell cycle. Furthermore, the RNA levels dropped significantly when the host cells reached confluency. This suggests that HCV RNA replication is tightly linked to host cell metabolism.

Although the HCV1b replicon developed by Lohmann et al. showed appreciable levels of RNA replication, this cell culture system was not efficient. The number of G418 resistance-colonies obtained after successful RNA transfection was consistently low and this low transduction efficiency limits its usefulness as a genetic tool.

To increase efficiency of the HCV1b replicon, Blight et al. (Blight et al., 2000), isolated and sequenced replicons from the Huh-7 cell clones and identified multiple independent adaptive mutations that cluster in the HCV NS5A ORF and bestowed increased replication competency in vitro. Transfection of the mutant HCV1b replicon conferred G418-resistant Huh-7 cells at a rate of 10%. The increase in the G418 transduction efficiency correlates with the level of replication measured with quantitative RT-PCR (Blight et al., 2000).

Due to the extensive genetic heterogeneity of HCV, it is desirable to develop self-replicating systems for more than one genotype. In an attempt to extend this system to other HCV genotypes, HCV genotype 1a-specific replicons were constructed according to the method used to provide HCV1b replicons. However, transfection of these HCV1a replicons failed to yield any G418-resistant colonies (Blight et al., 2000). Furthermore, engineering the most efficient adaptive mutations identified in the 1b replicon into the 1a-derived replicon did not yield detectable replication in Huh-7 cells.

To date, there have been no reports of an effective cell culture system for replication of HCV of subtype 1a.

Bukh's group at the N.I.H. (Yanagi, et al. 1997) constructed a stable full-length cDNA clone, H77C of HCV genotype 1a, strain H77. However, RNA derived from this construct is not an efficient replication system in cell culture. Nevertheless, this cDNA may be a useful source for HCV1a nucleic acids for use in an efficient biological model system for the study of HCV1a towards the development of vaccines and anti-viral drugs.

An estimated 200 million people are infected worldwide with HCV. As a consequence, HCV infection has emerged as a major public health problem. Therefore, basic molecular studies are necessary to define unique virological features for all HCV genotypes in general and subtype 1a in particular.

Developing a reliable cell culture system permissive for replication of HCV, including the HCV subgenotype 1a, has been elusive. There is an acute need to develop self-replicating systems for these genotypes of HCV which is addressed by the present invention.

SUMMARY OF THE INVENTION

The invention provides a Hepatitis C Virus (HCV) replicon that efficiently replicates in a eukaryotic cell. This HCV replicon includes a nucleic acid sequence encoding a genomic fragment of HCV and a nucleic acid sequence encoding an acetyl transferase selectable marker.

In another embodiment, the invention provides an HCV type 1a replicon that efficiently replicates in a eukaryotic cell. This HCV type 1a replicon includes a nucleic acid sequence encoding a genomic fragment of HCV and a nucleic acid sequence encoding an acetyl transferase selectable marker.

The invention further provides a eukaryotic cell line that includes a selectable HCV replicon that efficiently replicates in the eukaryotic cell. The eukaryotic cell line contains an HCV replicon that includes a nucleic acid sequence encoding a genomic fragment of HCV and a nucleic acid sequence encoding an acetyl transferase selectable marker.

Yet further, the invention provides a eukaryotic cell line that includes a selectable HCV subtype 1a replicon that efficiently replicates in the eukaryotic cell. The eukaryotic cell line contains an HCV subtype 1a replicon that includes a nucleic acid sequence encoding a genomic fragment of HCV subtype 1a and a nucleic acid sequence encoding an acetyl transferase selectable marker.

In yet another embodiment the invention provides a screening method for identifying a compound that inhibits the propagation of Hepatitis C Virus (HCV). The steps of the method are as follows:

(a) providing a cell line comprising an HCV replicon that efficiently replicates in the eukaryotic cell, wherein the replicon includes a nucleic acid sequence encoding a genomic fragment of HCV and a nucleic acid sequence encoding an acetyl transferase selectable marker;

(b) incubating the cell line with the compound in a growth medium that selects for the selectable marker under suitable conditions for growth of the cell line and assessing the growth of the cell line;

(c) providing an isogenic cell line that includes a replicon that efficiently replicates in the cell wherein the replicon comprises a replication origin that is not an HCV replication origin and a nucleic acid sequence encoding the acetyl transferase selectable marker, or an isogenic cell line comprising a nucleic acid sequence encoding the acetyl transferase selectable marker wherein the replicon does not include any HCV nucleic acid sequences;

(d) incubating the isogenic cell line with the compound in a growth medium that selects for the selectable marker under suitable conditions for growth of the isogenic cell line and assessing the growth of the isogenic cell line; and (e) comparing the growth assessed in (b) with the growth assessed in (d), wherein when the growth assessed in (b) is less than the growth assessed in (d), the compound is identified as a compound that inhibits the propagation of the HCV.

In yet a further embodiment the invention provides a screening method for identifying a compound that inhibits the propagation of Hepatitis C Virus (HCV) of subtype 1a. The steps of the method are as follows:

(a) providing a cell line that contains an HCV subtype 1a replicon that efficiently replicates in the eukaryotic cell, wherein the replicon includes a nucleic acid sequence encoding a genomic fragment of HCV subtype 1a and a nucleic acid sequence encoding an acetyl transferase selectable marker;

(b) incubating the cell line with the compound in a growth medium that selects for the selectable marker under suitable conditions for growth of the cell line and assessing the growth of the cell line;

(c) providing an isogenic cell line that includes a replicon that efficiently replicates in the cell wherein the replicon comprises a replication origin that is not an HCV replication origin and a nucleic acid sequence encoding the acetyl transferase selectable marker, or an isogenic cell line comprising a nucleic acid sequence encoding the acetyl transferase selectable marker wherein the replicon does not include any HCV nucleic acid sequences;

(d) incubating the isogenic cell line with the compound in a growth medium that selects for the selectable marker under suitable conditions for growth of the isogenic cell line and assessing the growth of the isogenic cell line; and (e) comparing the growth assessed in (b) with the growth assessed in (d), wherein when the growth assessed in (b) is less than the growth assessed in (d), the compound is identified as a compound that inhibits the propagation of HCV subtype 1a.

Also provided is a process for making a pharmaceutical compound useful for treating a Hepatitis C Virus infection. The process includes: providing a candidate pharmaceutical compounds; screening the candidate pharmaceutical compounds as described above; and preparing the identified candidate pharmaceutical compound manufactured under Good Laboratory Practice (GLP) conditions.

BRIEF DESCRIPTION OF THE FIGURES

FIG. 3. Schematic representation of (A) the HCV genome and (B) the subgenomic HCV replicon, HCV1a/pac.

FIG. 5. RT-PCR and PCR analysis of HCV1a/pac-containing Huh-7 cell clones. (A) RT-PCR analysis of total cellular RNA from a Huh-7 clone with NS5B-specicif primers. As control, RT-PCR reaction with naïve Huh-7 cellular RNA and without RNA template were included. M. DNA molecular weight marker III; T. RT-PCR of the respective transcript RNA. (B and C) Absence of integrated replicon DNA in cell clones selected under puromycin restriction. PCR from RNaseA-treated cellular DNA from a Huh-7 clone and naïve Huh-7 cells was preformed with NS5B-specific primers for panel B or with PAC-specific primers for panel C.

FIG. 6. In vivo $^3$H-labeling assay of HCV-specific RNA. (A) A series of naïve Huh-7 cells (open bars) and HCV1a/pac-containing Huh-7 cells (closed bars) in 6 cm culture dishes were preincubated with 5 μg/ml Actinomycin D for 1 hour before labeling with $^3$H-Uridine (50 μCi/ml) for various time as indicated. Total cellular RNAs were extracted at each time point and RNA synthesis was measured as radiolabeled uridine incorporated into RNA in the presence of Actinomycin D (1 μg/ml) by scintillation analysis. (B) Counts per minute (CPM) of RNA in replicon-containing Huh-7 cells was corrected by substraction of the CPM in naïve Huh-7 and converted to percentage of the maximal number of CPM.

DETAILED DESCRIPTION OF THE INVENTION

The present invention provides for the first time a selectable Hepatitis C Virus (HCV) replicon capable of efficiently replicating in a eukaryotic cell under conditions where selection is applied for an acetyl transferase selectable marker carried by the replicon.

The HCV replicons may be any HCV genotype or subtype including any of the HCV genotypes 1, 2, 3, 4, 5 or 6, each with two or more subtypes. The HCV replicon includes a nucleic acid sequence encoding a genomic fragment of the HCV and also a nucleic acid sequence encoding an acetyl transferase selectable marker.

The genomic fragment of the HCV may be any fragment of the HCV genome that provides the replicon with the ability to replicate the viral RNA in the eukaryotic cell into which it is transformed or transfected. The genomic fragment of the HCV may comprise any nucleotide sequence from the HCV genome. The fragment may comprise a single linear nucleotide sequence from the HCV genome, or the fragment may comprise two or more linear nucleotide sequences from the HCV genome. The two or more linear nucleotide sequences may be from contiguous or non-contiguous sequences within the HCV genome. For example, the HCV replicon HCV1a/pac of Examples 3–5 contains a sequence from the 5' end of HCV joined by intervening pac and EMCV sequences to another stretch of sequence encoding NS3-NS5B.

Selection of replication proficient replicon-containing cells is achieved when the viral RNA is translated to a polyprotein translation product which is properly processed to functional proteins that confer the ability to replicate the HCV sequences. The replicated HCV sequences also drive the transcription of the acetyl transferase selectable marker gene which is thereby transcribed. This translated acetyl transferase selectable marker gene transcript is then translated to provide a functional acetyl transferase that confers resistance to the selective drug.

The acetyl transferase selectable marker of the present invention may be any acetyl transferase that confers a selection on cells that express the marker, such as for instance the puromycin N-acetyl transferase selectable marker which confers resistance to exogenously added puromycin. Normally, cells are susceptible to inhibition of growth and ultimately to killing by puromycin in the growth medium. However, cells that express puromycin N-acetyl transferase are resistant to these effects and continue to grow. This forms the basis of the selection for cells expressing the selectable puromycin N-acetyl transferase marker from among sensitive cells that lack the marker, or fail to express the marker activity. This selection may be applied to select resistant cells from a mixed population of sensitive and resistant cells, even when the resistant cells are present in low numbers in a large population of sensitive cells. The selection may be used to select resistant cells present at a ratio of only one in a thousand, one in ten thousand, one in a hundred thousand or one in a million or more sensitive cells.

Thus, when the acetyl transferase is puromycin N-acetyl transferase, the HCV replicon-bearing eukaryotic cells that efficiently replicate are selected by the addition of puromycin to the cell growth medium. Puramycin may be used at any concentration from about 0.1 μg/ml to about 5 μg/ml to select for cells bearing efficiently replicating HCV replicons. Preferably the concentration of puramycin used for selection is from about 1 μg/ml to about 4 μg/ml. A concentration of puromycin of about 2 μg/ml has been found optimal for selection in human hepatoma cells.

In another embodiment, the invention provides a selectable HCV subtype 1a replicon capable of efficiently replicating in a eukaryotic cell under conditions where selection is applied for a acetyl transferase selectable marker carried by the replicon. In this embodiment where the replicon carries HCV type 1a nucleotides sequences, the selectable marker may be any acetyl transferase selectable marker.

The HCV replicons of the invention are capable of replicating efficiently in the selected eukaryotic cells. As used herein, efficient replication means that large number of cells in culture can be prepared that multiply rapidly, each cell carrying multiple copies (i.e. 100–1000 copies) of the replicons to produce sufficient amounts of acetyl transferase to inactivate the highly toxic drug used for selection. For example, the rapidly dividing cells may split twice per week. Further, efficient replication as used in the present specification means replication of the HCV replicon such that the HCV nucleic acid products are readily detectable without the use of polymerase chain reaction (PCR) for amplification. Alternatively, efficient replication as used herein means replication of the HCV replicon such that the HCV protein products expressed in the cell are readily detectable by western blot analysis. See for instance, Example 5.

Previously available methods for generating functional HCV replicons relied on selection with high concentrations of neomycin (500 $\mu$g/ml G418). It is possible that this high concentration is responsible for the inefficient replication of the HCV replicon type 1a by restraining the growth or proliferation of the cell or the HCV1a replicon as well as providing the necessary selective conditions. However, the replication of the HCV1b replicon is not so restrained by the high concentration of G418 (Lohmann et al., 1999).

The HCV replicons of the invention may be introduced into any eukaryotic cell type. Eukaryotic cells include cells from a mammal or a mammalian cell line; insect cells, such as for instance *Spodoptera frugiperda* cells; oocytes from any animal, such as for instance an amphibian, e.g. a frog or a toad (such as *Xenopus laevis*); or cells of a lower eukaryote, such as a yeast (e.g. the budding yeast, *Saccharomyces spp.*) or a filamentous fungus, such as for example, *Aspergillus spp.*

Mammalian cells useful in practicing the present invention include cells of rat, mouse, rabbit, dog, cat, sheep, goat, horse, cow, pig origin. Cells of primate origin are preferred. Primate cells of particular usefulness in the present invention include monkey, ape and human cells. Human cells are more preferable and human hepatoma cells are optimal.

Human cells are preferred as host cells for the HCV replicons of the present invention. The human cells may be any human cells or cell lines in which these HCV replicons of the present invention replicate. Human cell lines in which the replicons replicate, include for instance, hepatoma cell lines. Human hepatoma cell lines include for example, Huh-7 and HepG2. Alternatively, primary cell lines isolated from the intact organism, including human primary cell lines may also be used as the eukaryotic cells of the present invention in which the HCV replicon replicates.

HCV replicons of the present invention may be prepared from any HCV genotype or subtype. HCV genotypes detected to date include HCV genotypes 1, 2, 3, 4, 5 and 6, each with two or more subtypes. For example, HCV type 1 is divided into known subtypes 1a and 1b, and type 2 into subtypes 2a, 2b and 2c. Full length cDNA clones of each subtype may be prepared according to the methods used for the preparation of the HCV1a cDNA described below.

Generation of Full-Length cDNA of HCV type 1a.

Figure 1:
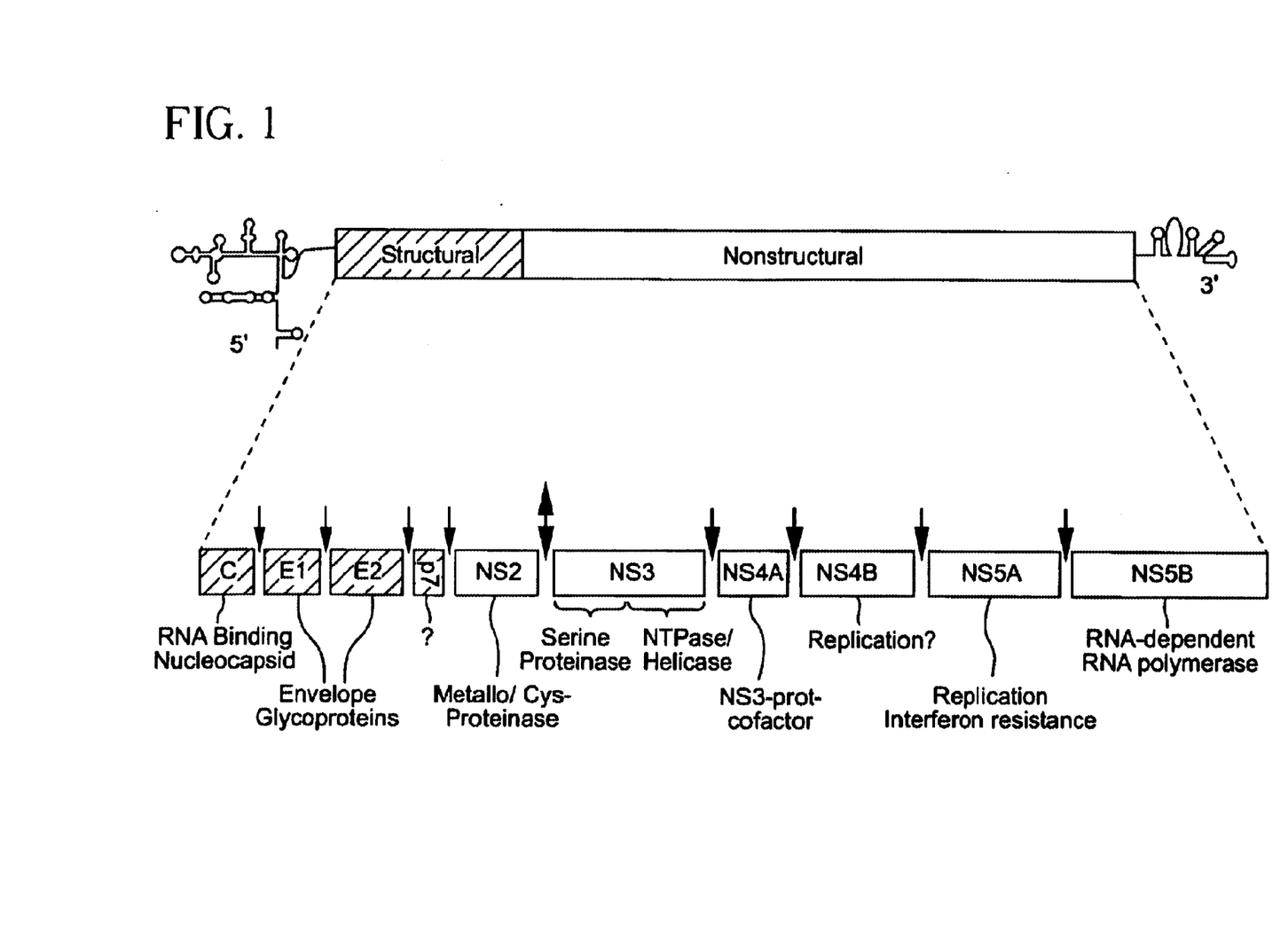
FIG. 1. is a schematic representation of the HCV genome (top) and polyprotein processing (bottom). The polypeptide cleavage sites are indicated by arrows. The functions of the different proteins (shown as blocks) are given below the protein blocks. A question mark indicates that the function is unknown.
Figure 2:
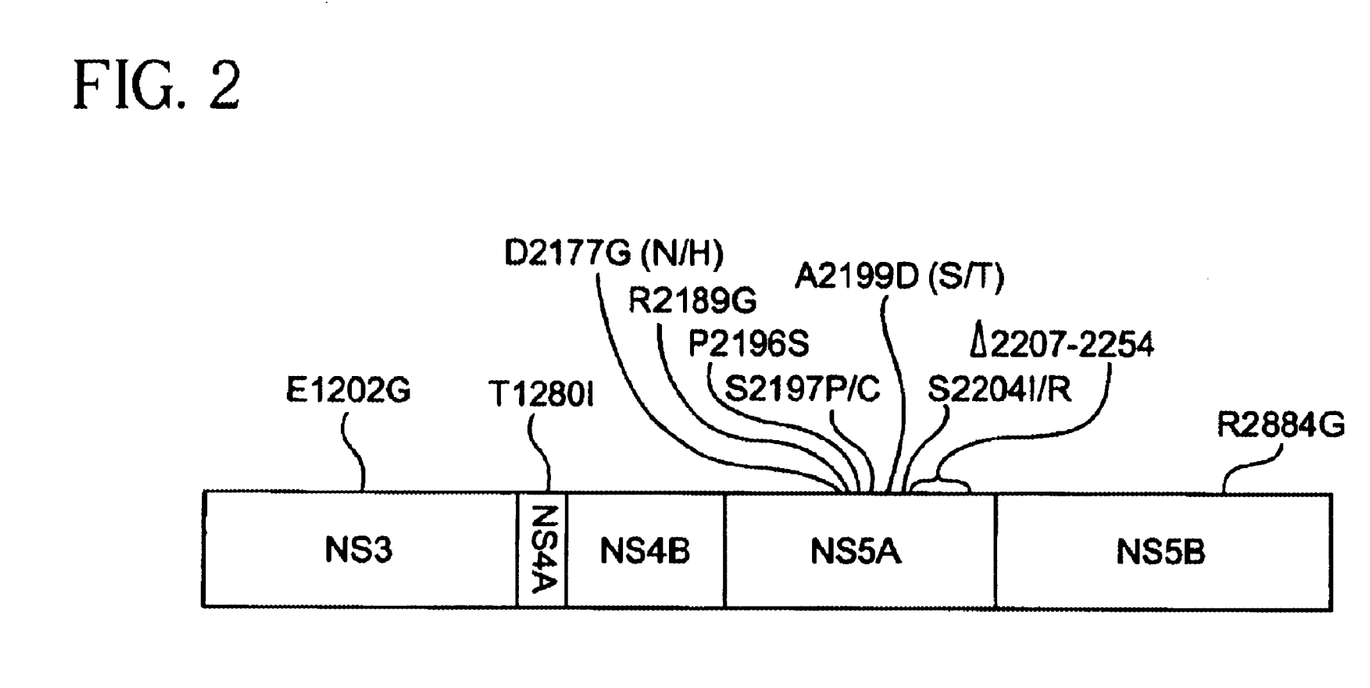
FIG. 2. Cell culture-adaptive mutations within the HCV NS3-5B coding region (Bartenschlager and Lohmann, 2001)

A full-length cDNA of HCV genotype 1a (see FIG. 1) is constructed according to the methods described in U.S. Pat. No. 6,153,421 to Yanagi et al., the specification of which is hereby incorporated by reference in its entirety. Briefly, plasma obtained from a patient infected with HCV type 1a is used to isolate viral RNA according to standard procedures. Primers are deduced from the genomic sequence of the viral RNA and utilized for reverse transcription and PCR. The overlapping DNA fragments obtained by PCR are assembled after fragmentation with the appropriate restriction enzymes. General recombinant DNA and cloning, expression and sequencing methods unless otherwise attributed may be found in Sambrook and Davies Eds., Molecular Cloning, Third Edition, 2001. Cold Spring Harbor Laboratory, Cold Spring Harbor Press, NY.

The full length cDNA is then cloned into a vector suitable for proliferation in bacterial cells. The full length cDNA may then be subjected to complete sequence analysis, and phage T7 transcriptase may be used to catalyze synthesis of full length plus strand viral RNA for preparation of HCV RNA. The virus-specific DNA of different clones may be prepared in this way and confirmed by sequencing. A consensus sequence is derived from the sequences of the different clones. This consensus sequence is then generated in a single clone by assembly of appropriate sub-fragments and site-directed mutagenesis. This generated cDNA may then be used as the source of HCV1a nucleic acid in the methods of the present invention to generate HCV1a replicons.

Hepatitis C virus cDNAs of other genotypes or subtypes are prepared in the same way, starting from viral RNA obtained from the plasma of a patient infected with the HCV of the genotype or subtype of interest.

Structural and nonstructural protein genes in the subgenomic fragment of the HCV replicon of the invention.

Figure 3A:
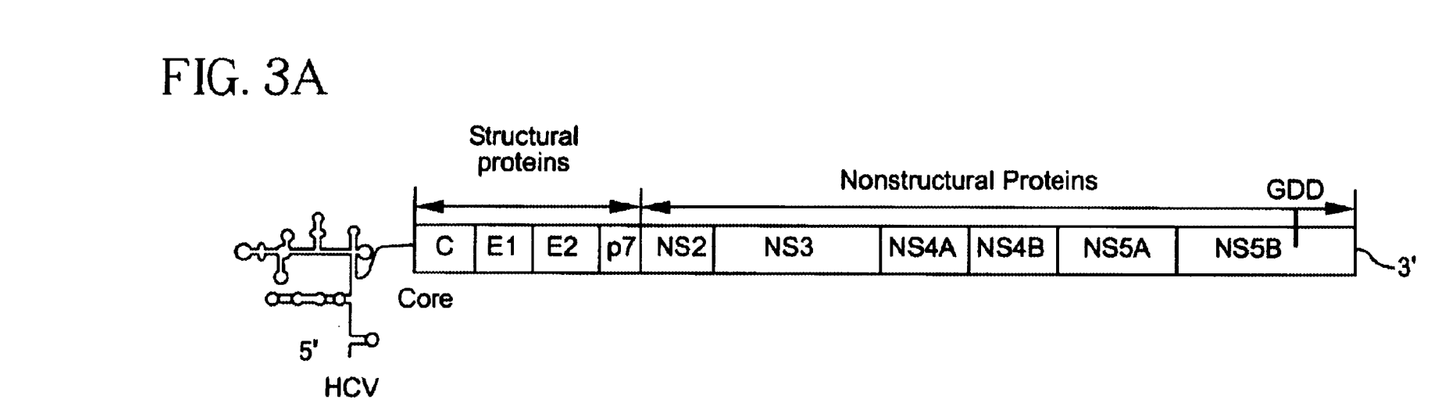
Figure 3B:
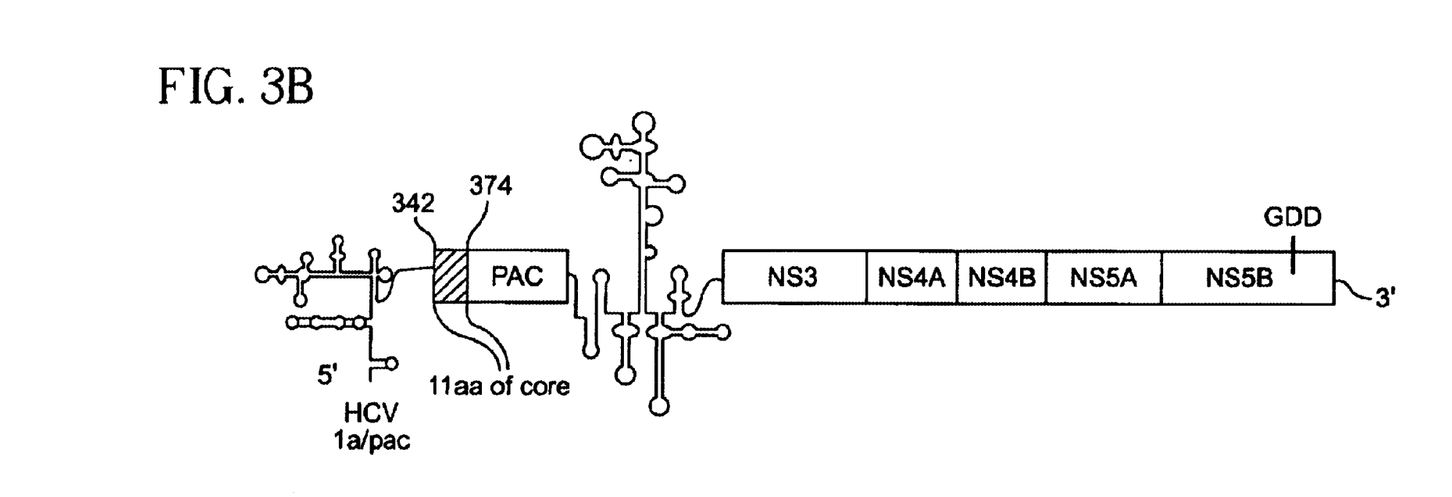

The full length cDNAs of any of the HCV genotypes prepared as described above are useful for the preparation of genomic fragments for incorporation into the replicons of the HCV present invention. The genomic fragments useful for incorporation into the replicons of the present invention include any nucleic acid fragment that confers replication function on the replicon in which it is incorporated. The minimal HCV nucleic acid sequence necessary to confer replication function includes the stretch of nucleotide sequence from NS3 (having serine proteinase activity and NTPase/helicase activity) at the 3' end and including NS4A (a NS3 proteinase cofactor), NS4B (a required replication function), NS5A (required for replication, and conferring interferon resistance) and NS5B (the RNA dependent RNA polymerase) at the 5' end. FIG. 3 depicts one such replicon, HCV1a/pac isolated as described in the Examples section below.

In addition to the indispensable NS3-NS5B region, the hepatitis C virus replicons of the invention may be extended in the 3' direction to also include the gene region encoding NS2. Processing of the primary polyprotein translation product to cleave between NS2 and NS3 to release active NS3 is required for efficient HCV replication.

In other embodiments, the genomic fragment of HCV in the replicon of the invention may extend further in the 3' direction of the HCV genome and in addition to the indispensable NS3-NS5B region, may incorporate nucleotide sequences encoding p7, or p7 and the envelope glycoprotein, E2. Yet further embodiments may also include p7, E2 and E1. In even yet further embodiments, the HCV replicon of the invention may extend over the entire structural region and may include p7, E2, E1 and the HCV RNA binding capsid, protein C. HCV proteins C (the RNA-binding capsid protein), the envelope glycoproteins E1 and E2A are structural proteins that are found in the HCV virion. For the purposes of this specification, p7 is defined as a structural protein, even though it is not present in the virion.

In another aspect the invention provides screening methods for identifying antiviral compounds that inhibit the propagation of HCV. The inhibition of HCV propagation may be by inhibition of replication, inhibition of processing of HCV proteins from the primary polyprotein translation product, or by inhibition of the RNA-dependent RNA polymerase or any other indispensable HCV activity that is required for replication of HCV RNA. For example, inhibition of an HCV specific protease activity responsible for cleavage of the HCV polyprotein may inhibit an HCV functional activity required for replication. Thus, for instance, inhibition of accurate processing of NS3 in an HCV replicon that includes the entire NS2 to NS5B region inhibits the formation of mature NS3 and thereby inhibits the HCV replication. Since processing of NS3 is necessary for replication, and replication is necessary for expression of the acetyl transferase selectable marker, the survival of the cell depends on processing of NS3 when the cell is grown under selective conditions.

The HCV replicon-bearing cells of the invention may be grown in any growth medium that supports the growth of the parent cell (without the HCV replicon) in the absence of a selection for the selective marker. Media for the growth and propagation of eukaryotic cells, especially mammalian cells in culture are well known in the art. An example of a commonly used growth medium for eukaryotic cells is Dulbecco's growth medium, DMEM. (See for instance, the Examples below). Selection of the selective marker is applied by adding an effective amount of the selective compound, such as for instance, puromycin.

When a test compound to be screened is added to the growth medium of the cell bearing the HCV replicon of the invention, in the event that the compound interferes with the function required for replication and hence expression of the selective marker, the growth of the cell in the presence of the compound will be inhibited or prevented altogether.

This level of growth is compared with the level of growth in the presence of the compound of an isogenic cell that carries a replicon that efficiently replicated in the isogenic cell, in which the replicon bears the same selective marker as the test cell described above, but replicates from an origin of replication that is not an HCV origin of replication. The control replicon that also bears the acetyl transferase selectable marker may be a replicon that replicates from a replication origin which is not an HCV replication origin, such as for instance a sindbis virus replication origin. In another alternative the control replicon may contain no HCV nucleotide sequences and therefore includes neither HCV protein functions nor an HCV origin of replication. Since the replication of such control replicons is neither dependent on the HCV replication origin, nor the HCV specific replication activities of the HCV proteins, the control cell provides a readout of the residual inhibitory effect of the test compound on all other functions required for cell growth.

Therefore, by comparison of the growth of the cell bearing the HCV replicon in the presence of the test compound with the growth of the control cell bearing a replicon that does not carry an HCV origin of replication, also in the presence of the test compound, the HCV-specific inhibitory effect of the compound may be assessed.

The growth of the cell bearing an HCV replicon encoding a acetyl transferase selectable marker, or a replicon encoding a acetyl transferase selectable marker that does not include an HCV origin of replication may be assessed by any of a number of known methods. The assessing of growth may be at a gross level of determination of growth versus no growth, giving a (+) or (−) readout.

Alternatively, and preferably, the growth may be assessed by a quantitative readout. This quantitative readout may be any quantitative readout of a function that is dependent on the growth of the cells that include the HCV replicon or the replicon that does not include an HCV origin of replication. For instance, cell density or cell number/ml of culture medium may be determined. In another alternative method for assessing the growth of the cells, an activity of a cellular function may be measured. The cellular function measured may be any cellular function that increases with growth of the cell. For instance, incorporation of $^3$H-nucleotides into nucleic acids, or incorporation of a $^3$H-amino acid into protein may be assessed as a monitor of growth of the cell. Other alternative readouts include for instance, colorimetric readouts, fluorescence readouts or luminescence readouts, each of which may be coupled to cellular functions necessary for growth.

Compounds which cause inhibition of growth of the cell bearing the HCV replicon may do so by inhibiting the propagation of the HCV replicon. The compounds that achieve this are candidates for inhibitors of HCV replication.

Compounds that may be screened for anti-HCV antiviral activity are small molecules or biological molecules. Biological molecules include all lipids and polymers of monosaccharides, amino acids and nucleotides having a molecular weight greater than 450. Thus, biological molecules include, for example, oligosaccharides and polysaccharides; oligopeptides, polypeptides, peptides, and proteins; and oligonucleotides and polynucleotides.

Biological molecules further include derivatives of any of the molecules described above. For example, derivatives of biological molecules include lipid and glycosylation derivatives of oligopeptides, polypeptides, peptides and proteins. Derivatives of biological molecules further include lipid and glycosylated derivatives of oligosaccharides and polysaccharides, e.g. lipopolysaccharides.

Any molecule that is not a biological molecule is considered in this specification to be a small molecule. Accordingly, small molecules include organic compounds, organometallic compounds, salts of organic and organometallic compounds, saccharides amino acids, and nucleotides. Small molecules further include molecules that would otherwise be considered biological molecules, except their molecular weight is not greater than 450. Thus, small molecules may be lipids, oligosaccharides, oligopeptides, and oligonucleotides, and their derivatives, having a molecular weight of 450 or less.

It is emphasized that small molecules can have any molecular weight. They are merely called small molecules because they typically have molecular weights less than 450. Small molecules include compounds that are found in nature as well as synthetic compounds.

Compounds which inhibit the propagation of HCV identified by the methods described herein are lead compounds for anti-HCV antiviral drug development. These compounds are anti-HCV antiviral hits or lead compounds which may be optimized by screening of libraries of analogs and related compounds and tested in any available HCV model systems and ultimately in humans in clinical trials.

Compounds which inhibit the propagation of HCV identified by the methods described herein are lead compounds for anti-HCV antiviral drug development. These compounds may be optimized for antiviral activity by screening libraries of analogs of the lead compounds and related compounds. Analogs or related compounds with superior antiviral characteristics may be tested in any available HCV model system and ultimately in humans in clinical trials.

Initial so-called Phase I clinical trials are designed to assess safety of the compound in a small number, often between twelve and twenty healthy volunteers. These initial small scale trials may require compound preparation under a level of stringency referred to as Good Laboratory Practice (GLP). Upon demonstration of successful Phase I trials, more stringent requirements for preparation of the compound under Good Manufacturing Practice (GMP) is necessary so that a clinical grade of the compound may be tested in a safety and efficacy trial in a population that has or may have the condition (in this case an HCV infection) for which the new drug treatment is to be tested.

EXAMPLES

Example 1

Synthesis of a Subgenomic HCV1a Replicon Expressing Puromycin N-acetyltransferase (HCV1a/pac)

H77C infectious HCV1a clone pCV(H77C) was constructed according to the methods described in U.S. Pat. No. 6,153,421, the specification of which is hereby incorporated by reference in its entirety.

The HCV1a replicon includes the following genetic elements: the HCV 5'NTR plus approximately 33 nucleotides of the HCV core ORF, which is referred to as the HCV IRES (nucleotides 1–374), the puromycin N-acetyltransferase gene (PAC), the encephalomyocarditis virus (EMCV) internal ribosome entry site (IRES), HCV sequences from NS3 through NS5B, including NS4A, NS4B, and NS5B, and the 3' non translated region.

The IRES (nucleotides 1–374) of HCV was amplified by polymerase chain reaction and inserted into a pSK(−) vector (Stratagene, La Jolla, Calif.) that was pre-treated with the restriction endonucleases Kpn I and Bam HI (New England Biolabs, Mass.) to provide a linear vector with two different restriction endonuclease overhang sequences for cloning Kpn I-Bam HI fragments.

The puromycin N-acetyltransferase gene (PAC) was amplified by PCR using the pPUR vector (Clontech, Palo Alto, Calif.) as a template. The amplified PAC was then ligated to the HCV IRES to generate pSK-HCV IRES-PAC.

Next, nucleotides encoding HCV NS3-4A was ligated to nucleotides encoding the IRES of EMCV and inserted into a plasmid vector to generate pEMCV IRES-HCV NS3-4A.

The EMCV IRES-HCV NS3-4A DNA was then ligated to the HCV IRES-PAC DNA to obtain HCV IRES-PAC-EMCV IRES-HCV NS3-4A DNA and introduced into a fragment of pCV(H77C) containing nucleotide sequences encoding NS4B, NS5A, NS5B, and the HCV 3'NTR to engineer the dicistronic HCV1a replicon, which is composed of HCV IRES-PAC-EMCV IRES-HCV NS3-4-5-HCV 3'NTR (FIG. 3B).

The HCV1a replicon is designated HCV1a/pac. The PAC gene permits positive selection for Huh-7 cell clones in which replication of the subgenomic RNA has occurred. The EMCV IRES provides for efficient translation of the downstream viral NS genes.

Example 2

HCV1a/pac Transfection of Huh-7 Cells

Subconfluent Huh-7 cells were trypsinized, washed twice with phosphate buffered saline, and resuspended in Cytomix buffer (van den Hoff et al., 1992) containing 1.25% dimethyl sulfoxide (DMSO) at a density of $10^7$ cells/ml. 400 µl of cell suspension was placed in an electroporation cuvette (0.4 cm gap width; Bio-Rad, Munich, Germany) and 1 to 5 µg of in vitro-transcribed replicon RNA (HCV1a/pac) was added. The in vitro-transcribed RNA was prepared by cutting the plasmid containing the sequence for the HCV1a/pac replicon at an Xba I site with the Xba I restriction endonuclease (New England Biolabs, Beverly, Mass.) to linearize the DNA, followed by transcription with phage T7 RNA polymerase that recognizes a promoter at the left end of the linearized DNA. At the end of the incubation, the reaction mixture was treated with DNase I to remove the template DNA.

The cells were then subjected to one or two electric pulses at 960 µF and 0.27 kV using a Gene pulser system (Bio-Rad, Munich, Germany). A derivative of HCV1a/pac carrying a lethal mutation in NS5B RNA dependent RNA polymerase (HCV1a/pol⁻) served as a negative control. Following electroporation, the cell suspension is diluted into 7 ml of DMEM containing 10% fetal bovine serum and 1.25% DMSO and seeded onto a 10 cm diameter Petri dish.

Figure 4:
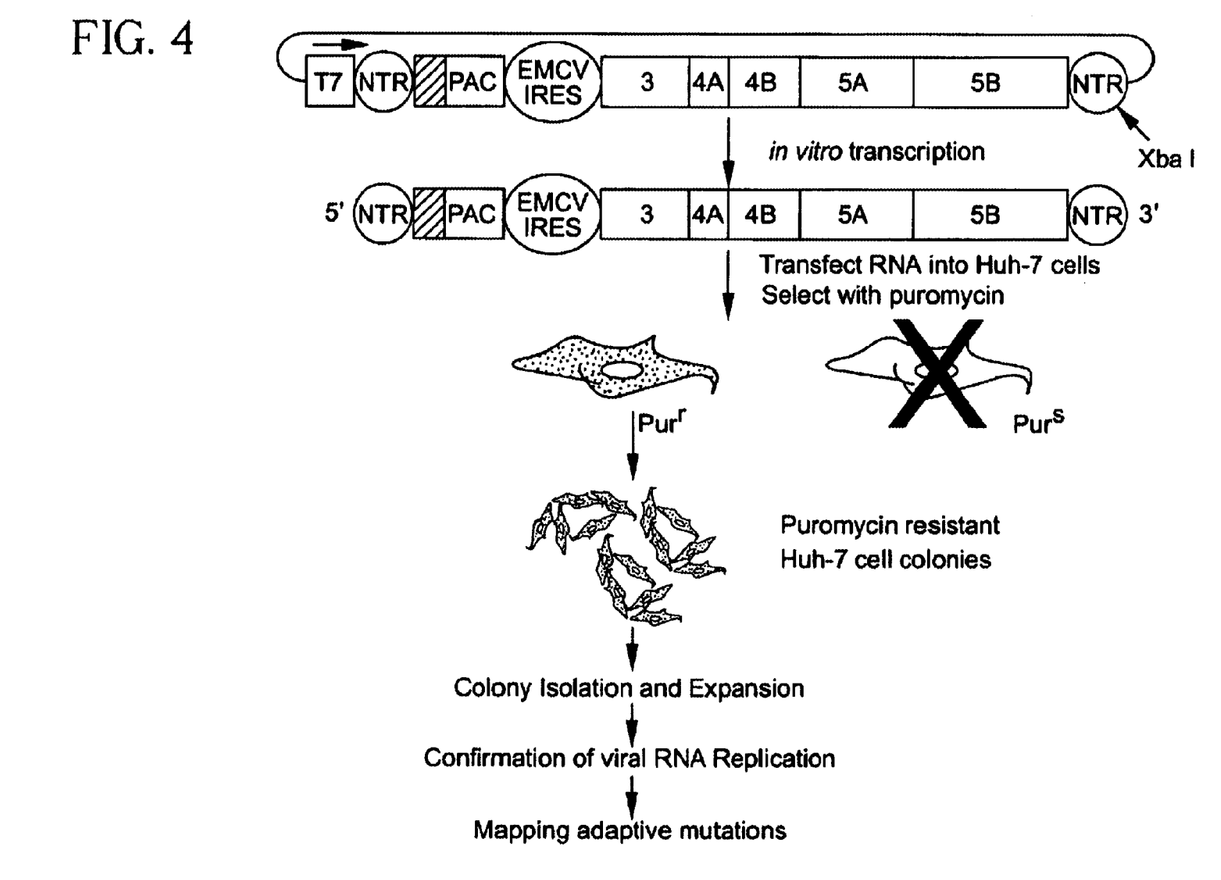
FIG. 4. Schematic of strategy used for positive selection of Huh-7 cell lines carrying self-replicating HCV RNAs.

After 24 hours in culture, the medium in the 10 cm dish was replaced with DMEM cell culture medium (Gibco-BRL, Rockville, Md.) supplemented with 10% fetal bovine serum and puromycin (2 µg/ml) and changed every three days. See FIG. 4., which depicts the strategy used for positive selection of Huh-7 cell lines carrying self-replicating HCV RNAs.

Approximately 20 to 200 colonies were obtained when Huh-7 cells were transfected with 1 µg of in vitro-transcribed RNA (HCV1a/pac) and as expected, no colonies were observed after transfection with HCV1a/pol⁻ RNA.

Thirty of the HCV1a/pac transformed Huh-7 colonies were isolated and expanded into cell lines for further analysis. These selected cell lines exhibited a slight retardation in growth compared with wild type Huh-7 cells, but appeared normal by high-power light microscopy without observable signs of cytopathic effect under these conditions. This distinguishes the HCV replicon from the replicons of other RNA viruses such as bovine viral diarrhea virus (BVDV) which are associated with a delayed but still profound cytopathic effect during replication in mammalian cells. The apparent absence of a cytopathic effect makes the HCV replicon particularly useful for studies of the mechanism of replication as well as long-term expression of foreign genes.

Example 3

Detection of HCV1a/pac-Specific RNA by RT-PCR in Cells Resistant to Puromycin

Figures 5A, 5B:
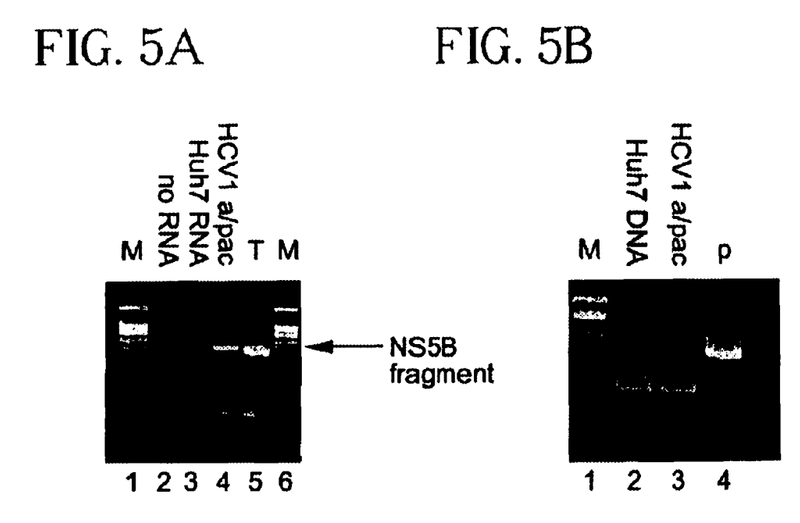
Figure 5C:
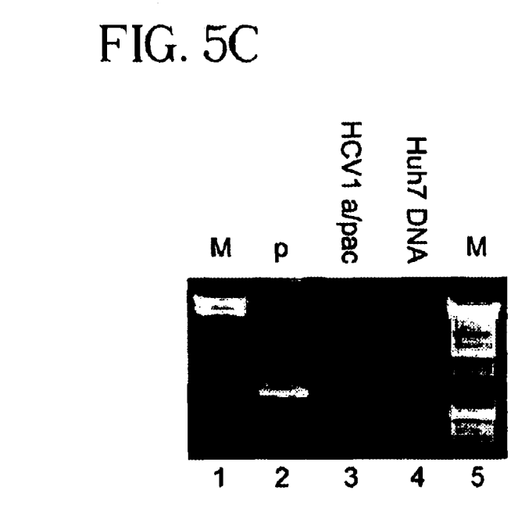

The Huh-7 cell lines that were transformed with HCV1a/pac were maintained in medium with puromycin (2 µg/ml) for up to 3 months and analyzed by RT-PCR with NS5B-specific primers. DNA fragments of the expected size (1.4 kb) were detected for the samples containing viral RNA but not for the control, which contained no viral RNA (FIG. 5A). The observed amplification products could not have resulted from carry-over of plasmid DNA or from integration of plasmid DNA into the host cell genome since a direct PCR assay of total cellular DNA with NS5B-specific and PAC-specific primers bypassing the step of reverse transcription did not yield a positive PCR product (FIGS. 5B and 5C). This provided unambiguous evidence that puromycin resistance cell clones contain HCV RNA but not HCV-specific DNA.

Example 4

Actinomycin D Resistant Accumulation of HCV1a/pac RNA

Figure 6A:
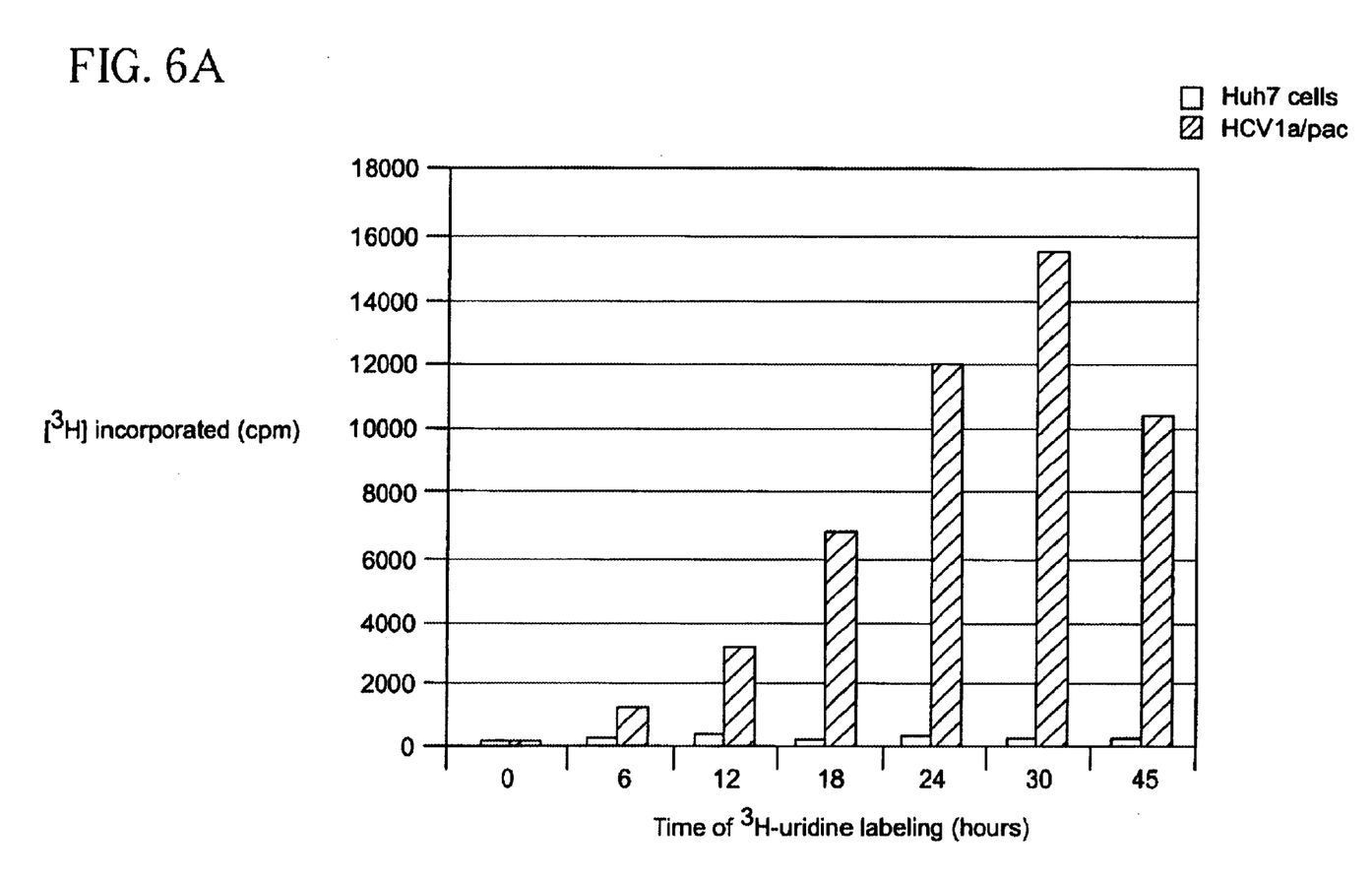
Figure 6B:
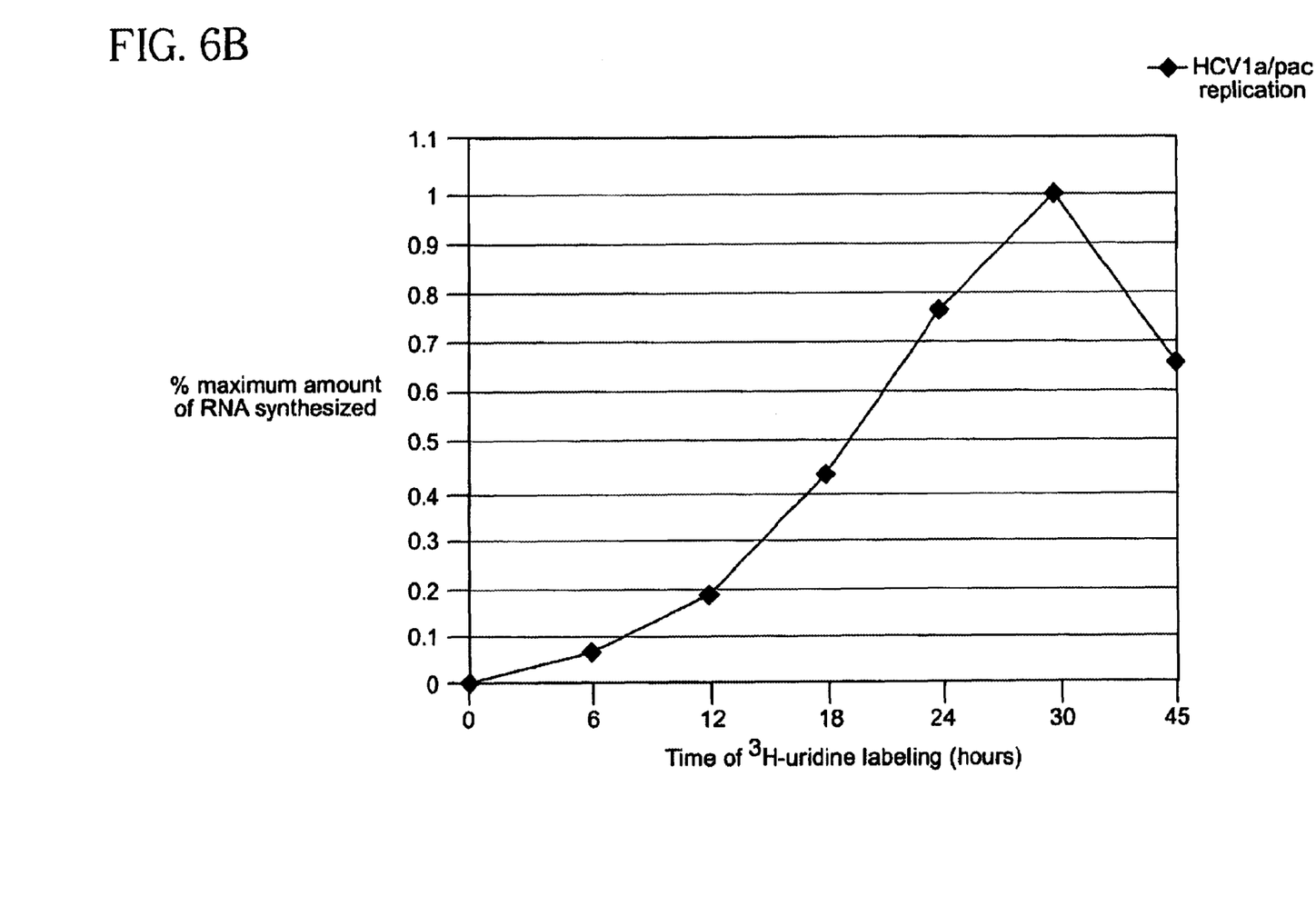

Cells that were passaged twice a week in the presence of puromycin were seeded in multiple cell culture plates and pretreated for 1 hour with 5 µg/ml actinomycin D, an antibiotic that selectively inhibits RNA synthesized from DNA templates. After treatment with actinomycin D, the cells were incubated with [$^3$H] uridine (in the presence of 1 μg/ml of actinomycin D). At each time point, cells were harvested and labeled RNAs were isolated using the TRIzol reagent (Gibco-BRL, Rockville, Md.). [$^3$H] uridine incorporation was analyzed by scintillation counting. The level of HCV specific RNA in selected cells increased approximately seven fold during the first 30 hours of incubation and dropped sharply thereafter (FIG. 6). The drop is most likely due to actinomycin D-induced host cell death that limited host cell factors required for replicon RNA translation and replication.

Accumulation of [$^3$H]-labeled RNAs was observed in the cell lines selected with puromycin, whereas synthesis of cellular RNAs was blocked. This data demonstrates that the RNAs were generated by the HCV NS5B, the HCV-specific RNA-dependent RNA polymerase, rather than by cellular DNA-dependent RNA polymerases.

Example 5

HCV1a/pac Replicon Yields Hepatitis C Virus-specific Proteins

Whole cell lysates of HCV1a/pac-containing cell lines were separated on a 10% SDS-polyacrylamide gel and examined for putative HCV NS3 and NS5B antigens by Western blot analysis with NS3-specific or NS5B-specific monoclonal antibodies. Proteins of the appropriate sizes (70 kDa for NS3 and 65~68 kDa for NS5B) were observed in extracts derived from HCV1a/pac-containing cell lines. No reactivity with either antibody was detected with lysates prepared from naïve Huh-7 cells.

Indirect immunofluorescence analysis of HCV NS3, NS5B proteins in parental and replicon-containing cells was performed as previously described by Pietschmann et al. (Pietschmann et al., 2001). In brief, cells grown as monolayer on microscope cover slides were fixed in an ice-cold mixture of methanol and acetone (1:1), then incubated for 1 hour in immunofluorescence buffer (PBS, 3% BSA, 0.1% Triton X-100) at 4° C. Primary antibody was added in immunofluorescence buffer. Bound primary antibody was detected with a fluorescein isothiocyanate-conjugated goat anti-mouse immunoglobulin. Fluorescence was observed using a fluorescence microscope.

No immunofluorescence was observed in the Huh-7 cells. However, punctuate perinuclear as well as diffuse cytoplasmic fluorescence was visible in the HVC 1a/pac replicon-containing Huh-7 cells, demonstrating the expression of HCV1a-specific proteins.

REFERENCES

Bartenschlager, R., Lohmann, V. 2001. Novel cell culture systems for the hepatitis C virus. *Antiviral Research.* 52:1–17.

Bartenschlager, R., Lohmann, V. 2000. Replication of hepatitis C virus. *J. of Gen. Virol.* 81:1631–1648.

Blight, K. J., Kolykhalov, A. A., Rice, C. M. 2000. Efficient initiation of HCV RNA replication in cell culture. *Science.* 290, 1972–1974.

Bukh, J., Miller, R. H., and Purcell, R. H. 1995. Genetic heterogeneity of hepatitis C virus: quasispecies and genotypes. *Semin. Liver Dis.* 15, 41–63.

Dash, S., Halim, A. B., Tsuji, H., Hiramatsu, N., Gerber, M. A. 1997. Transfecting of HepG2 cells with infectious hepatitis C virus genome. *Am. J. Pathol.* 151, 363–373.

Farci, P., Bukh, J., and Purcell, R. H. 1997. The quasispeies of hepatitis C virus and the host immune response. *Springer Semin. Immunopathol.* 19, 5–26.

Lohmann, V., Korner, F., Koch, J. O., Herian, U., Theilmann, L., Bartenschlager, R. 1999. Replication of subgenomic hepatitis C virus RNAs in a hepatoma cell line. *Science.* 285, 110–113.

Southern, P. G., and P. Berg. 1982. Transformation of mammalian cells to antibiotic resistance with a bacterial gene under the control of the SV40 early region promoter. *J. Mol. Appl. Genet.* 1, 327–341.

van den Hoff, M. J., A. F. Moorman, and W. H. Lamers. 1992. Electroporation in 'intracellular' buffer increases cell survival. *Nucleic Acids Res.* 20:2902.

Yanagi, M., Purcell, R. H., Emerson, S. U., and Bukh. J. 1997. Transcripts from a single full-length cDNA clone of hepatitis C virus are infectious when directly transfected into the liver of a chimpanzee. *Proc. Natl. Acad. Sci. USA* 94, 8738–8743.

Zein, N. N., and D. H. Persing. 1996. Hepatitis C genotypes: current trends and future implications. *Mayo Clin. Proc.* 71, 458–462.

Zein, N. N., J. Rakela, E. L. Krawitt, K. R. Reddy, T. Tominaga, D. H. Persing, and the Collaborative Study Group. 1996. Hepatitis C virus genotypes in the United States: epidemiology, pathogenicity, and response to interferon therapy. *Ann. Intern, Med.* 125, 634–639.

What is claimed is:

1. A Hepatitis C Virus (HCV) 1a replicon that efficiently replicates in a human hepatoma cell, wherein the replicon comprises a genomic fragment of HCV1a, wherein the genomic fragment comprises:
   (i) the HCV1a 5' non-translated region plus approximately 33 nucleotides of the open reading frame of HCV1a core protein gene fused in frame to a nucleic acid sequence encoding a puromycin N-acetyl transferase gene;
   (ii) an encephalomyocarditis IRES linked to HCV1a genes NS3, NS4A, NS4B, NS5A and NS5B; and
   (iii) the 3' non-translated region of HCV1a.

2. An HCV1a replicon according to claim 1 which is HCV1a/pac.

3. An HCV1a replicon according to claim 1, wherein the human hepatoma cell is a Huh-7 cell.

4. An HCV1a replicon according to claim 1, wherein the human hepatoma cell is a HepG2 cell.

5. A human hepatoma cell line comprising an HCV1a replicon according to claim 1.

6. A human hepatoma cell line according to claim 5, wherein the HCV1a replicon is HCV1a/pac.

7. A human hepatoma cell line according to claim 5, wherein the human hepatoma cell is a Huh-7 cell.

8. A human hepatoma cell line according to claim 5, wherein the human hepatoma cell is a HepG2 cell.

9. A screening method for identifying a compound that inhibits the propagation of Hepatitis C Virus (HCV) 1a comprising:
   (a) providing a human hepatoma cell line comprising an HCV1a replicon according to claim 1;
   (b) incubating the cell line with the compound in a growth medium that selects for puromycin resistance under suitable conditions for growth of the cell line and assessing the growth of the cell line;
   (c) providing an isogenic cell line comprising a replicon that efficiently replicates in the isogenic cell wherein the replicon comprises a replication origin that is not an HCV1a replication origin and a nucleic acid sequence encoding the puromycin N-acetyl transferase gene, or an isogenic cell line comprising a nucleic acid sequence 
encoding the puromycin N-acetyl transferase gene wherein the replicon does not comprise any HCV1a nucleic acid sequences;

(d) incubating the isogenic cell line with the compound in a growth medium that selects for puromycin resistance under suitable conditions for growth of the isogenic cell line and assessing the growth of the isogenic cell line; and (e) comparing the growth assessed in (b) with the growth assessed in (d); wherein when the growth assessed in (b) is less than the growth assessed in (d), the compound is identified as a compound that inhibits the propagation of HCV1a.

10. A screening method according to claim 9, wherein the HCV1a replicon is HCV1a/pac.

11. A screening method according to claim 9, wherein the human hepatoma cell is a Huh-7 cell.

12. A screening method according to claim 9, wherein the human hepatoma cell is a HepG2 cell.

* * * * *